United States Patent [19]

McConnell et al.

[11] Patent Number: 4,927,424
[45] Date of Patent: May 22, 1990

[54] REAMER GUIDE FOR INTRAMEDULLARY NAIL PLACEMENT

[76] Inventors: Bernard E. McConnell, Rte. 2, Box 87; John C. McConnell, 614 Mink Dr., both of Greenville, Tex. 75401

[21] Appl. No.: 224,451
[22] Filed: Jul. 26, 1988
[51] Int. Cl.⁵ ............................................. A61B 17/56
[52] U.S. Cl. ..................................... 606/96; 606/102
[58] Field of Search ........ 128/92 VD, 92 VL, 92 VJ, 128/92 V; 141/329, 330, 358; 606/96, 102, 104

[56] References Cited

U.S. PATENT DOCUMENTS

| | | | |
|---|---|---|---|
| 4,409,973 | 10/1983 | Neufeld | 128/92 VD X |
| 4,678,471 | 7/1987 | Noble et al. | 128/92 VD X |
| 4,686,972 | 8/1987 | Kurland | 128/92 V |
| 4,800,875 | 1/1989 | Ray | 128/92 V |

FOREIGN PATENT DOCUMENTS 1260077  2/1968  Fed. Rep. of Germany ........ 128/92 VD

OTHER PUBLICATIONS

Mueller & Co. Advertisement, Scuderi–Callahan Flange Director, 2-15-38, Surg. Gyn. & Obs. p. 11.
Wisconsin Med. Journal, L. Littig, Article 5/1939.
Defrey Mfg. Catalog, Littig Nail Guide pp. 52–53, 1943.
Int. Abstract of Surgery 1944 vol. 77, p. 529.
Zimmer Mfg. News Release, 9/1966.

Primary Examiner—Robert A. Hafer
Assistant Examiner—Kevin G. Rooney
Attorney, Agent, or Firm—Dennis T. Griggs

[57] ABSTRACT

A guide apparatus for orthopedic surgery provides locational guidance for insertion of an orthopedic nail through a pilot bore into the intramedullary canal of a fractured bone. The guide creates a protected channel through soft tissue which shields the soft tissue from contact by a reaming tool and prevents soft tissue from interfering with a reaming procedure. The guide collects marrow and bone fragments, removed during reaming to prevent their dispersion in soft tissue. Bone fragments and marrow collected on the guide are reintroduced into the canal for grafting. The apparatus includes an elongated chute having a concave, arcuate segment terminating at a spooned end adapted to be mounted controllably spaced in alignment with the pilot bore. An elongated pin secured to the backside of the chute extends beyond the spooned end of the chute for insertion into the proximate bone area. Both guide apparatus and method of utilizing the guide apparatus are disclosed.

4 Claims, 3 Drawing Sheets

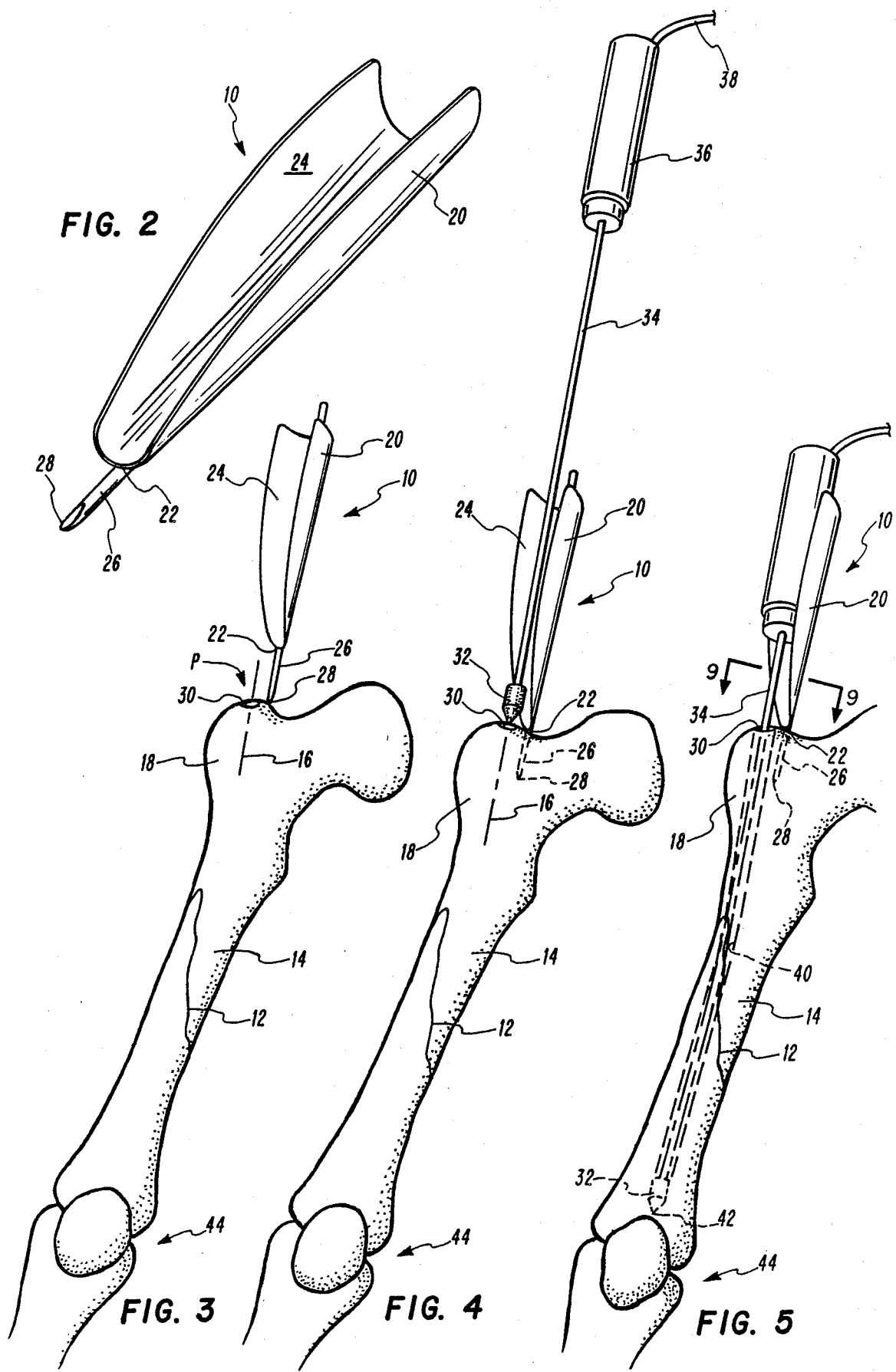

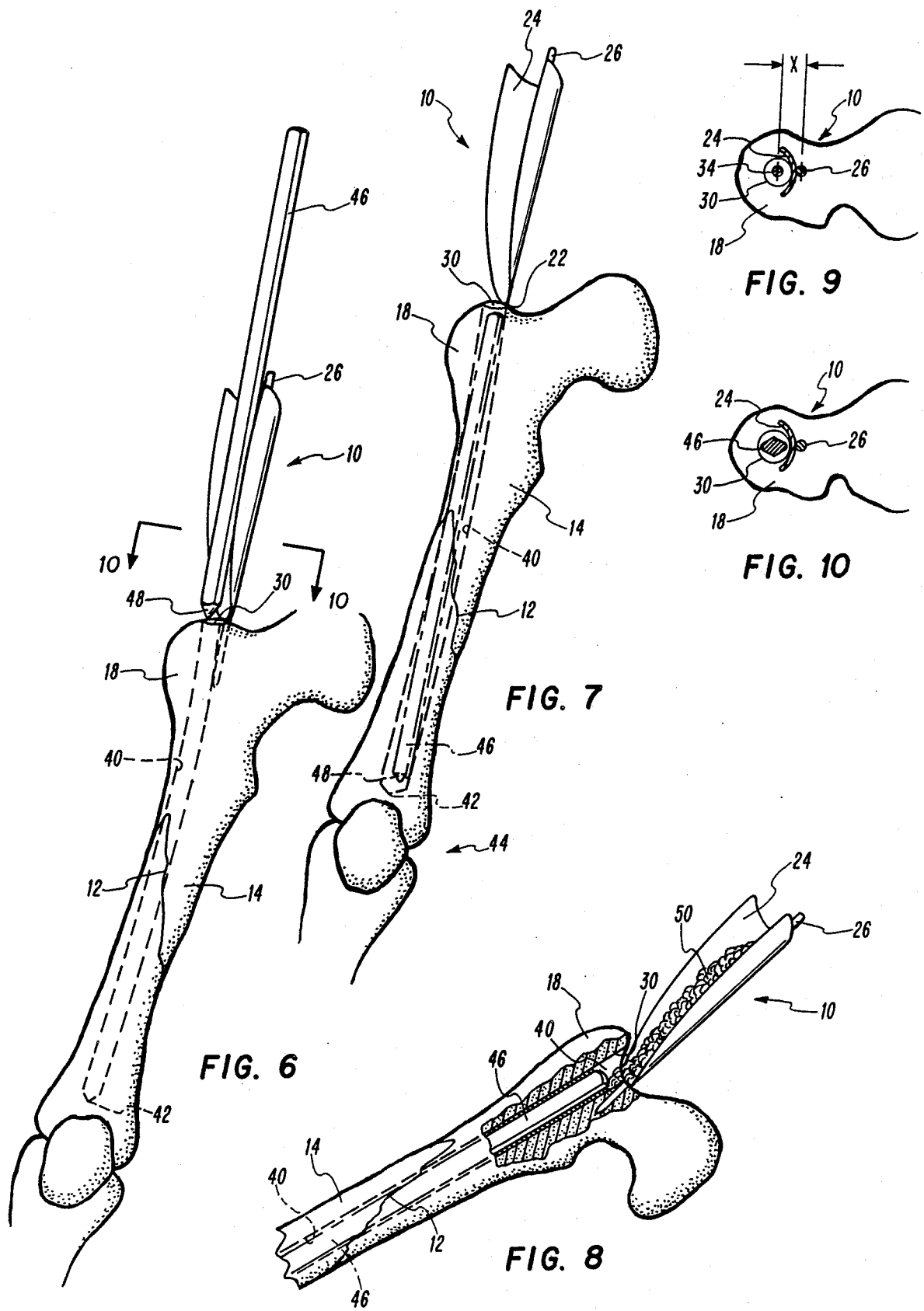

4,927,424

REAMER GUIDE FOR INTRAMEDULLARY NAIL PLACEMENT

FIELD OF THE INVENTION

This invention relates to the art of orthopedic surgery for repairing bone fractures utilizing intramedullary nails.

BACKGROUND OF THE INVENTION

It is customary in repair and setting of bone fractures to secure the fractured sections together with the use of a rod or nail placed in the intramedullary canal. Spanning the fracture zone, the rod imposes a rigidity to the fracture area that could otherwise be difficult to maintain during the prolonged period of mending. When left permanently in place, the rod reinforces the bone and reduces its susceptibility to refracture.

DESCRIPTION OF PRIOR ART

Rod or nail placement in the intramedullary canal for securing bone fractures is a common practice in orthopedic surgery. Use of the rod is known to inherently produce better healing in more extreme fractures than other procedures in which the rod is omitted. Preliminary to placement of the rod or nail, the procedure typically requires an incision followed by drilling of a pilot hole at the entrance of the canal. By inserting a reamer bit of progressively increasing size through the entrance opening, the canal is reamed repetitively in successive steps until the canal is enlarged sufficiently to receive the rod. Reaming is commonly effected in ½ millimeter increments. Before insertion of the rod, withdrawn bone fragments are returned to the canal.

Repeated insertion placement of the reaming instrument into the entrance opening is conducted by a hand. In the course of the procedure it is highly desirable for the entrance opening leading to the intramedular cavity to be accurately approached. This serves to minimize unnecessary overenlargement of the opening and consequent damage to surrounding tissue. The repetitive accuracy by which the reaming procedure is accomplished has of necessity resided with the skill of the surgeon. However, because of the delicate nature of the procedure, approach accuracy can prove both difficult and troublesome particularly when dealing with obese or highly muscular patients in which cancellous bone fragments tend to lodge in gluteus muscle tissue. Even after the canal has been cleared it is desirable to insert the nail with the same degree of approach accuracy in order to avoid any unnecessary disturbance to the surrounding bone and tissue.

OBJECTS OF THE INVENTION

It is therefore an object of the invention to provide a guide apparatus useful for providing instrument guidance in the repetitive reaming of an intramedullary canal for rod placement in the repair of a bone fracture.

A yet further object of the invention is to provide a guide apparatus to serve as a visual aid to surgeon accuracy when inserting a rod or nail into the entrance opening of a canal cavity.

It is a still further object of the invention to provide a guide apparatus that also serves to restrain surrounding tissues removed from the entrance opening while the surgical procedure is being conducted.

It is a still further object of the invention to provide a funnel or guide to permit reintroduction of bone fragments into an intramedullary canal for purposes of bone grafting while a surgical procedure is being conducted.

SUMMARY OF THE INVENTION

This invention relates to a guide apparatus useful in providing a reference surface for visually and mechanically guiding a surgical reamer into an entrance opening of an intramedullary canal of a fractured bone to be nailed. More specifically, the invention relates to a guide apparatus useful not only for guiding the reamer during each penetrating reinsertion into the canal opening, but which also serves to concomitantly restrain surrounding tissues to protect these tissues during reaming and provide similar guidance to insertion of the nail after clearing of the canal has been completed. The guide apparatus also serves to permit collection of bone particles removed during reaming and to serve as a guide and funnel to permit reintroduction of these particles for purposes of bone grafting.

The foregoing objects are achieved in accordance with the preferred embodiment of the invention by means of a guide apparatus having an elongated troughed chute that in transverse section defines an arcuate segment. The chute is of predetermined internal radius and length merging to a spooned tip at one end adapted to be placed proximate to the bone. For mounting the chute in place there is secured to the backside of the chute an elongated pin extending beyond the placement end of the chute for insertion into adjacent bone. When mounted, the chute extends in a generally parallel orientation to the entrance opening but controllably spaced therefrom in a guiding relation to the entrance opening.

Once the guide is mounted in place, its curved interior surface defines a reference surface for rendering visual and mechanical guidance to placement of the reamer tip on repetitive reamer reinsertion during which the intramedullary canal is progressively enlarged. Moreover, the guide when secured in place also restrains surrounding tissue from the surgical area during the entire procedure and allows collection of bone fragments removed during reaming. Once cavity clearing is completed, the interior curved reference surface of the guide affords similar directional guidance for the nail to be inserted. Before nail insertion and prior to removal, the guide serves as a dispenser chute for returning removed marrow and cancellous bone fragments to the canal for purposes of bone grafting.

The foregoing features and advantages of the invention as well as other superior aspects thereof will be further appreciated by those skilled in the art upon reading the detailed description which follows in conjunction with the drawings.

BRIEF DESCRIPTION OF THE DRAWINGS

FIG. 2 is a perspective view of the guide apparatus of the invention;

FIGS. 3, 4 and 5 are elevation views of the femur bone in FIG. 1 illustrating the step sequence for clearing the intramedullar canal preparatory to insertion of a supporting nail;

FIGS. 6 and 7 are elevation views sequentially illustrating nail insertion into the femur bone of FIG. 1;

FIG. 8 is a fragmentary view partially sectioned of the intramedullary nail placement in the reamed canal of a femur bone illustrating restoration of removed bone marrow and cancellous bone fragments to the canal cavity;

FIG. 9 is a sectional view taken along the lines 9—9 of FIG. 5; and,

FIG. 10 is a sectional view taken along the lines 10—10 of FIG. 6.

DESCRIPTION OF THE PREFERRED EMBODIMENT

Figure 1:
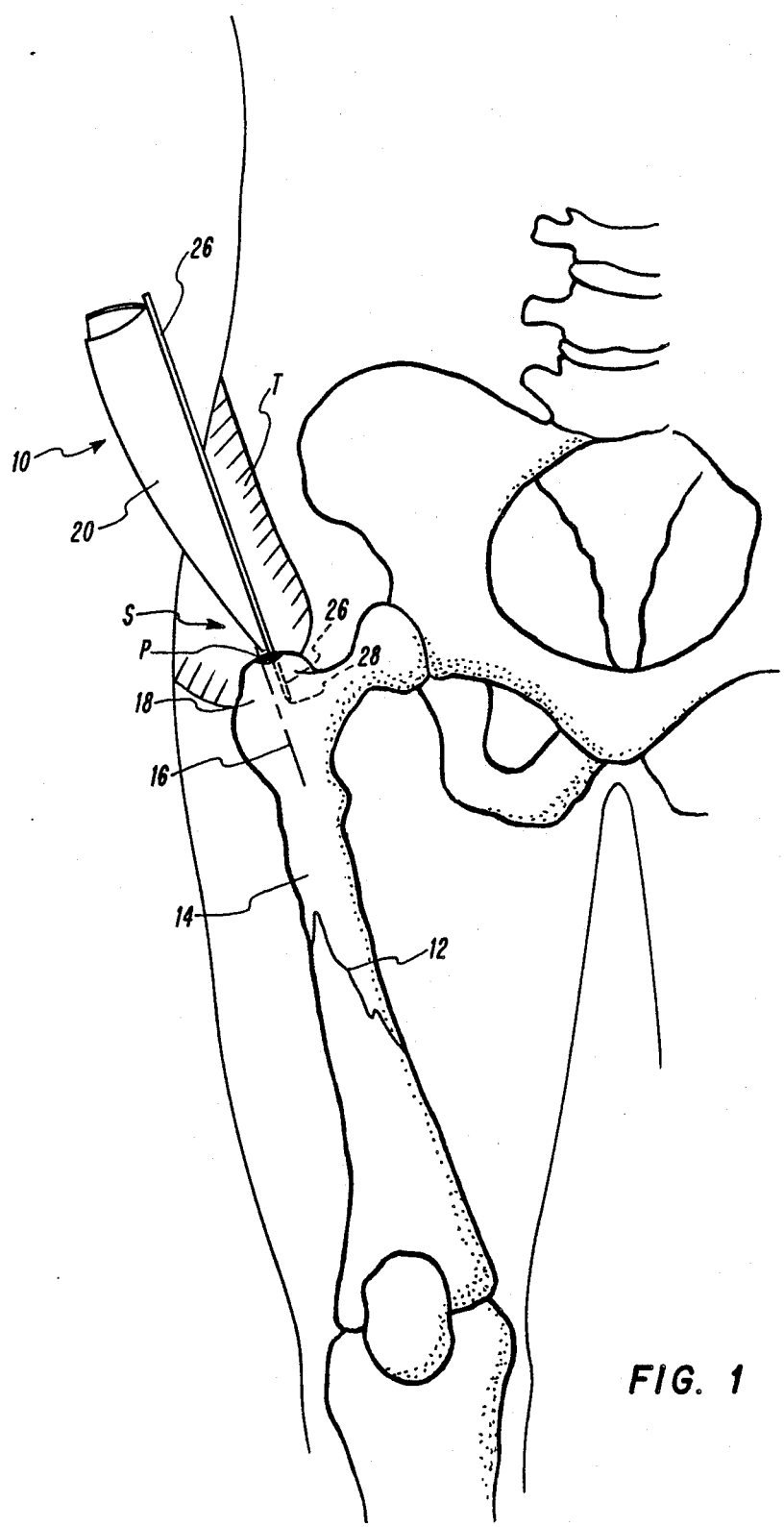
FIG. 1 is an elevation view of a fractured femur bone exemplifying use of the guide apparatus of the invention.

In the description which follows, like parts are marked throughout the specification and drawings with the same reference numerals, respectively. The drawing figures are not necessarily to scale and the proportions of certain parts have been exaggerated for purposes of clarity.

Referring now to the drawings, the reamer guide apparatus of the present invention is designated 10 and is illustrated in connection with repairing the fracture 12 in a femur bone 14. To approach the intramedullar cavity preliminary to clearing the canal, an incisions is first made in tissue T after which a pilot bore P is drilled along centerline 16 on the medial side of the greater trochanter 18.

Comprising guide 10 hereof for providing visual guidance to the pilot bore P is an elongated metal chute having a curved, open shell 20. The shell 20 is shaped in section as an arcuate segment and terminates at its placement end in a spoon-like nose 22. The interior concave surface 24 of the shell is smoothly finished of predetermined selected radius as will be understood. Secured to the back sidewall of shell 20 is an elongated pin 26 terminating as a sharp point at its distal end 28 extending beyond chute nose 22.

After the initial pilot bore P has been drilled, the drill bit is removed leaving only the surface entrance 30 visible to the surgeon for the subsequent steps to be performed. To provide visual guidance for enhanced accuracy during repeated entering entrance opening 30 in connection with the progressive reaming steps which ensue, point 28 of guide pin 26 is inserted into the trochanter 18 within a carefully controlled proximate distance "X" therefrom. Penetration of pin 26 is continued until causing the nose 22 to engage the trochanter surface with interior spoon surface 24 openly facing toward entrance opening 30. This renders the installed guide upright with pin 26 being in a generally parallel orientation with respect to the axis 16 of the pilot bore P and entrance opening 30.

Thereafter, reaming of the intramedullary canal 40 (FIG. 5) is initiated by a conically pointed reamer 32 supported for rotation on the end of a small diameter flexible shaft 34. The shaft and reamer are driven by an air motor 36 to which compressed air is supplied via conduit 38. The shaft and reamer may also be driven by other motorized instruments such as electrically powered motors.

With each reinsertion of a reamer 32, locational guidance to opening 30 is provided by visual comparison to the curved reference surface 24. The entire length of intramedullar canal 40 (FIG. 5) is repetitively reamed by progressively larger sized reamer bits 32 to a predetermined depth location 42 above the knee joint 44. For these purposes, placement of pin 26 relative to opening 30 is preferably of a dimension "X" such that the radius of curvature of the entrance opening 30 when fully enlarged will be substantially equal to the radius of curvature of the internal curved surface 24 of the guide chute (FIG. 9, FIG. 10).

During reaming of the canal 40, the internal curved surface 24 serves to collect marrow and bone fragments removed during reaming and prevent dispersion of this material into surrounding tissue.

After the intramedullary canal has been sufficiently enlarged to the desired size, the elongated metal rod or nail 46 having a pointed end 48 is inserted into entrance opening 30 in the manner illustrated in FIG. 6. The nail 46, which may have a diamond or other cross-section as shown in FIG. 10, is initially oriented parallel to the interior surface of chute surface 24 and is then forced inwardly past the fracture 12 to the reamed end 42 of the canal. Prior to insertion of nail 46, bone fragments and marrow 50 removed during the drilling and reaming steps are collected onto the chute surface 24 for a dispensing restoration into the canal 40 (FIG. 8). On completion of the latter, nail 46 is introduced inwardly past the fracture 12 to rearward end 42 of the canal. Guide 10 is then removed and disposed of and/or alternatively sterilized for reuse.

By the above description there is disclosed a novel guide apparatus particularly useful in orthopedic surgery in preparing a fractured bone for receipt of an intramedullary nail. The guide apparatus 10 is relatively simple in construction yet by virtue of its configuration and its ability to be placed parallel and closely spaced to the intramedullary canal, provides a visual reference and mechanical guide for the reamer as it is repetitively inserted into the canal opening. With chute end 22 engaging the trochanter surface 18 when installed, the curved chute sidewall 20 substantially restrains the surrounding tissue T behind the guide 10 so as to avoid tissue interference during the repetitive reinsertion placement of the reamer and permits injury to soft tissue. The chute end 22, curved shell sidewall 20 and curved surface 24 collect marrow and bone fragments and prevent their dispersion into surrounding soft tissue. Having been accurately placed with respect to the circumference of the ultimate enlargement opening 30 effected by the reamer 32, the guide 10 also provides similar guidance to the nail 46 during the course of its insertion. Moreover, guide 10 serves as a dispenser for restoring withdrawn bone fragments and marrow to the cleared canal cavity 40. While seemingly simple in relation to the surgery to which it relates, the function the guide 10 performs is important in the visual guidance and enhanced accuracy it provides to the orthopedic surgeon.

Since many changes could be made in the above construction and different embodiments of this invention could be made without departing from the scope thereof, it is intended that all matter contained in the drawings and specification shall be interpreted as illustrative and not in a limiting sense.

We claim:

1. Orthopedic surgery apparatus for guiding extension and retraction of a reaming tool through an opening defining an entrance to the intramedullary canal of a fractured bone, said apparatus comprising, in combination:

an elongated guide chute having an open shell defining a trough which is concave in cross section, and having a nose portion adapted for placement adjacent to said entrance opening against the surface of a fractured bone; and, an elongated pin attached to said shell, said elongated pin having a piercing end portion projecting in alignment with the longitudinal axis of said elongated guide chute, said piercing end portion being adapted for insertion into the bone in the proximate vicinity of said entrance opening for securing said chute in longitudinal alignment with said intramedullary canal.

2. In the method of clearing an intramedullary canal of a fractured bone into which a reinforcing nail is to be inserted for reinforcing the fractured region, including the steps of effecting an opening in the bone defining an entrance into said canal extending generally coaxially therewith and progressively reaming said canal with a reamer tool to incrementally enlarge the canal sufficiently to receive a nail to be inserted within the canal, the improvement comprising:

during the reaming step, guiding longitudinal movement of the reaming tool along an elongated guide chute having an open shell which is concave in cross section, and which has an elongated pin secured to said shell;

inserting a piercing end portion of the elongated pin into the fractured bone adjacent to the entrance opening;

positioning said elongated guide chute in longitudinal alignment with said canal; and, retracting adjacent tissue against the exterior curved surface of said shell as the reamer tool is advanced into and withdrawn out of the intramedullary canal.

3. The method as defined in claim 2, including the step of inserting the piercing end portion of the pin adjacent to the entrance opening at a spacing distance such that the radius of curvature of the entrance opening when fully enlarged by a reaming tool will be substantially equal to the radius of curvature of the concave curved surface of the guide chute.

4. The method as defined in claim 2, including the step of collecting bone marrow and fragments removed during the reaming steps within the concave shell while engaging the surrounding tissue with the external curved surface of the shell during the collecting step, thereby avoiding tissue interference during repetitive placement, insertion and withdrawal of the reamer tool and preventing dispersion of the collected marrow and bone fragments into the surrounding soft tissue.

* * * * *